United States Patent [19]
Cheng

[11] Patent Number: 5,131,192
[45] Date of Patent: Jul. 21, 1992

[54] DUST ARRESTER FOR A SANDING MACHINE

[76] Inventor: Mau-Nan Cheng, No. 161-7, Chung-Shan Rd., Feng-Yuan City, Taichung Hsien, Taiwan

[21] Appl. No.: 793,816

[22] Filed: Nov. 18, 1991

[51] Int. Cl.$^5$ .................................... B24B 55/06
[52] U.S. Cl. ........................ 51/273; 144/252 A; 55/DIG. 18
[58] Field of Search ............ 51/268, 270, 273, 166 R, 51/166 FB; 144/252 R, 252 A; 15/352, 301; 55/310, 311, 338, DIG. 18

[56] References Cited
U.S. PATENT DOCUMENTS
3,808,750 5/1974 Mann .................................... 51/273

FOREIGN PATENT DOCUMENTS
0246321 9/1947 Switzerland ...................... 51/273
0679388 9/1952 United Kingdom ............... 51/273

*Primary Examiner*—Roscoe V. Parker
*Attorney, Agent, or Firm*—Brooks & Kushman

[57] ABSTRACT

A dust arrester for a sanding machine includes a hollow workbench and a tubular filter unit which is axially rotatable inside the hollow workbench. A suction unit draws polluted air into the workbench to be filtered by the filter unit. A blowing unit is disposed inside the filter unit and generates a downwardly oriented air stream to blow dust particles collected by the filter unit into a removable dust receiving bin inside the workbench. The dust arrester is simple in construction, has a relatively low cost, and can effectively control air pollution.

5 Claims, 8 Drawing Sheets

DUST ARRESTER FOR A SANDING MACHINE

BACKGROUND OF THE INVENTION

1. Field of the Invention

The invention relates to a dust arrester, more particularly to a dust arrester for a sanding machine.

2. Description of the Related Art

Tiny dirt particles are produced whenever a sanding machine is used to smooth or polish the surface of a metal or wooden workpiece. These dirt particles pollute the surrounding environment and can be harmful to one's health. At a time when environmental pollution is taken seriously into account, it is highly desirous to improve the present working environment by making it cleaner and healthier.

A dust arrester is used to collect the tiny particles produced when performing a sanding operation. In a first kind of conventional dust arrester, one side of the housing of this dust arrester is provided with a suction conduit. The suction conduit is communicated with the air outside the workshop. A suction unit is then used to draw the dirt particles into the suction conduit. Dirt particles inside the suction conduit are collected by a dust handling means which is provided near one end of the suction conduit. This kind of a dust arrester has a relatively high cost and is ineffective in controlling air pollution.

In a second kind of conventional dust arrester, a plurality of dust collecting pipes are provided inside the housing of the dust arrester. A passage connects the bottom ends of the dust collecting pipes. A suction unit and a motor are provided on one side of the housing. The motor actuates the suction unit to draw air through the dust collecting pipes and into the passage. Dirt particles are collected on the walls of the dust collecting pipes. After a period of use, a vacuum unit (the suction force of which is greater than that of the suction unit) is used to draw the dirt particles from the dust collecting pipes for the collection thereof in a dust receiving bin. Although this kind of dust arrester is more effective in controlling air pollution, it requires the use of a vacuum unit and thus has a relatively higher cost.

SUMMARY OF THE INVENTION

Therefore, the main objective of the present invention is to provide a dust arrester for a sanding machine which can effectively control air pollution at a relatively lower cost.

Accordingly, the preferred embodiment of a dust arrester of the present invention comprises:

a hollow workbench including: a confining wall that defines a receiving space and having an open top end, a front side and a rear side; an upright mounting plate provided inside the confining wall between the front side and the rear side, the mounting plate partitioning the receiving space into a first chamber and a second chamber, the mounting plate being formed with an enlarged through opening; a diametrically extending positioning plate of predetermined width being mounted on the mounting plate at the through opening; a tabletop including a hollow loop frame mounted on the open top end of the confining wall and having an inner periphery, and a flat table surface mounted on the inner periphery of the loop frame, the table surface having a perforated portion disposed directly on top of the first chamber, the loop frame confining an air passage and having a notch communicating the second chamber and the air passage, and an elongated outlet communicating the air passage and the surrounding atmosphere; a removable dust receiving means provided at a bottom end of the first chamber; and a sound damping unit provided inside the second chamber at the rear side of the confining wall;

a tubular filter unit being provided inside the first chamber and including a tubular filter net having a closed end and an open end, and an annular mounting portion provided on the open end of the filter net and being rotatably mounted on the mounting plate around the through opening;

a first driving unit provided inside the first chamber and axially rotating the filter unit;

a second driving unit mounted to the positioning plate and extending into the filter unit, the second driving unit having a front output shaft and a rear output shaft, the rear output shaft extending into the second chamber through the positioning plate;

a blowing unit being provided inside the filter unit and having a downwardly oriented air outlet with an elongated mouth that extends in the axial direction of the filter unit, the blowing unit further having a fan blade being rotated by the front output shaft of the second driving unit so as to generate an air stream at the air outlet to blow dust particles collected by the filter net into the dust receiving means; and a suction unit being provided inside the second chamber and having a fan blade rotatably driven by the rear output shaft of the second driving unit so as to draw polluted air into the first chamber via the perforated portion of the table surface.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
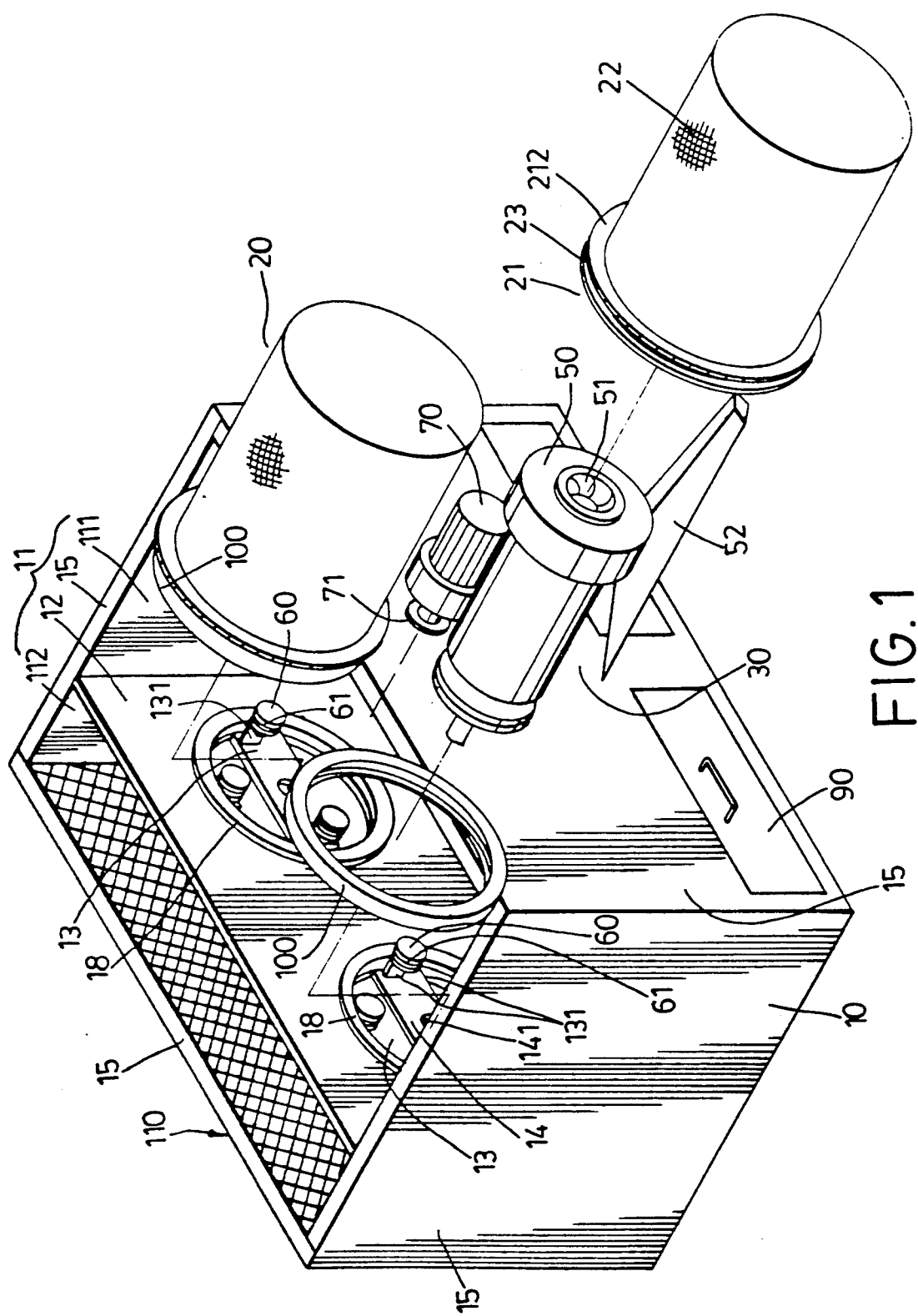
FIG. 1 is a fragmentary exploded view of the first preferred embodiment of a dust arrester according to the present invention.
Figure 2:
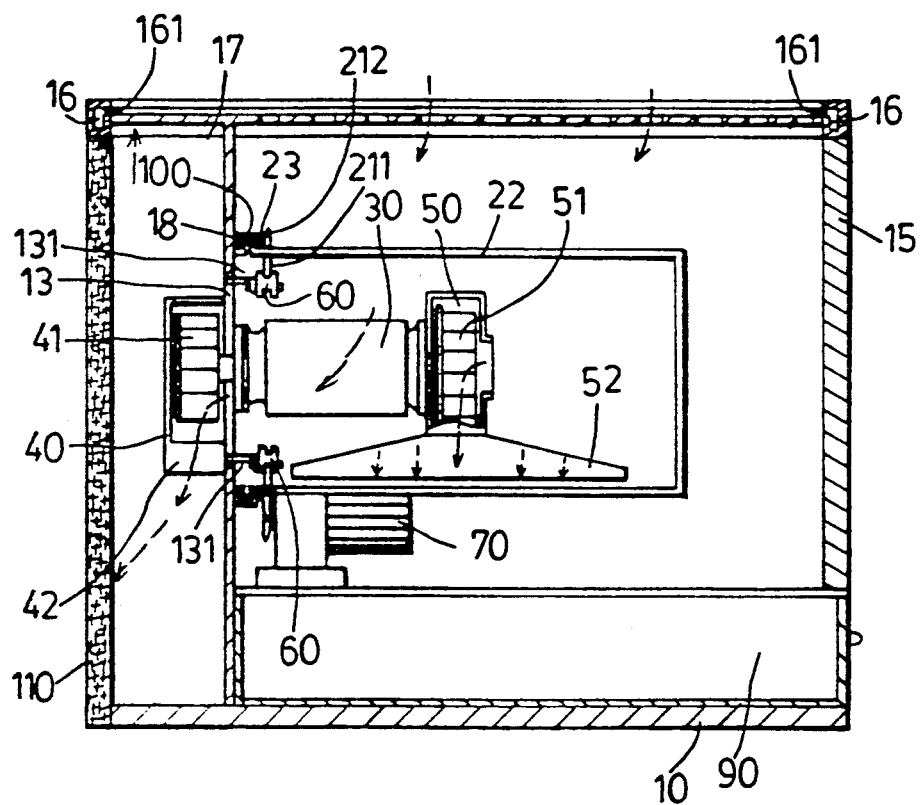
FIG. 2 is a side view of the dust arrester of the first preferred embodiment.
Figure 3:
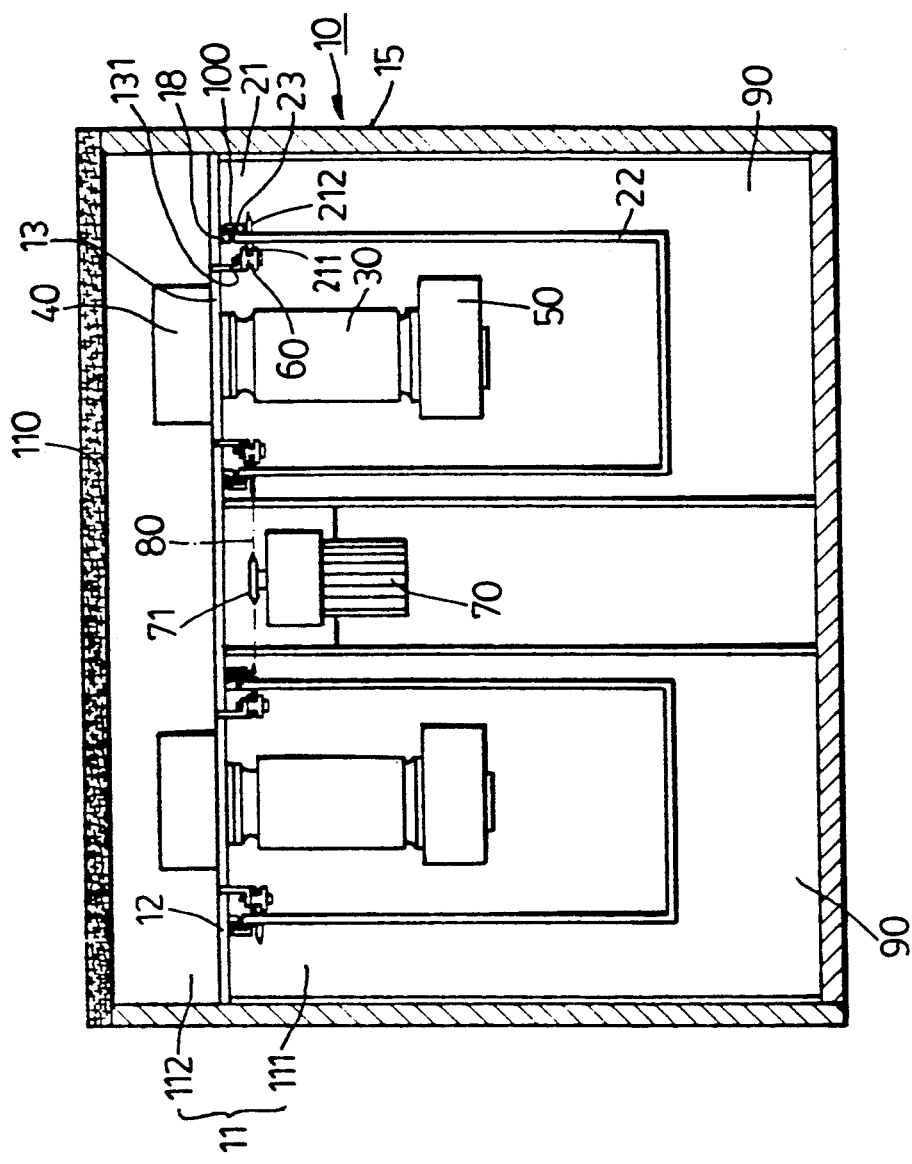
FIG. 3 is a top view of the first preferred embodiment.
Figure 3A:
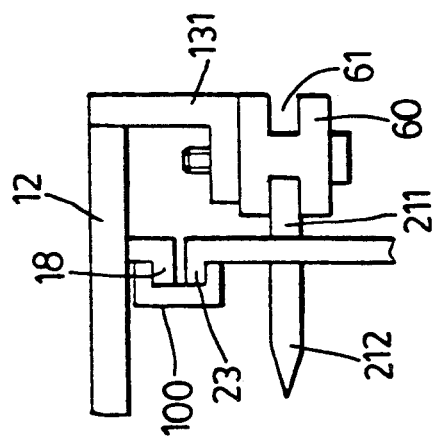
FIG. 3A is an enlarged view illustrating how a filter unit is rotatably mounted on an upright mounting plate of the first preferred embodiment.
Figure 4:
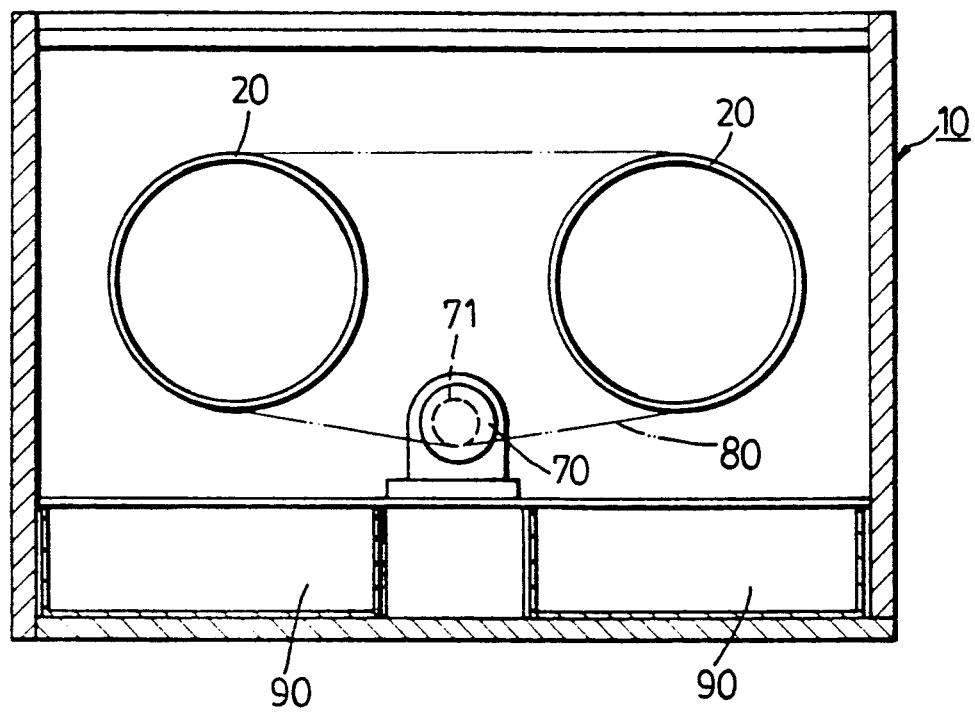
FIG. 4 is a front view of the first preferred embodiment of a dust arrester according to the present invention.

Referring to FIGS. 1 to 5, the first preferred embodiment of a dust arrester according to the present invention is shown to comprise a hollow workbench (10), at least one filter unit (20), at least one driving unit (30), at least one suction unit (40) and at least one blowing unit (50).

The size of the workbench (10) can be varied according to the desired area of dust arresting. The workbench (10) has four confining walls (15) that define a receiving space (11). The receiving space (11) is partitioned by an upright mounting plate (12) into a larger chamber (111) and a smaller chamber (112). A driving unit (70) is provided inside the receiving space (11) at a lower end of the larger chamber (111) and is secured to the mounting plate (12). The driving unit (70) has an output shaft provided with a sprocket (71). The workbench (10) is further provided with a pair of drawer-type dust receiving bins (90) associated with a front one of the confining walls (15) and slidably extending into the larger chamber (111). The dust receiving bins (90) are disposed on two sides of the driving unit (70).

The mounting plate (12) is formed with at least one through opening (13) and is shown provided with two through openings (13) in FIG. 1. Four equally spaced ears (131) project inwardly into the larger chamber (111) from the periphery defining each of the through openings (13). A bearing member (60) is mounted on each ear (131) and is provided with a peripheral groove (61). The mounting plate (12) is further provided with an annular step portion (18) disposed around each of the through openings (13). Each of the through openings (13) is provided with a diametrically extending positioning plate (14) of predetermined width. The positioning plate (14) is formed with a central axle hole (141).

Figure 5:
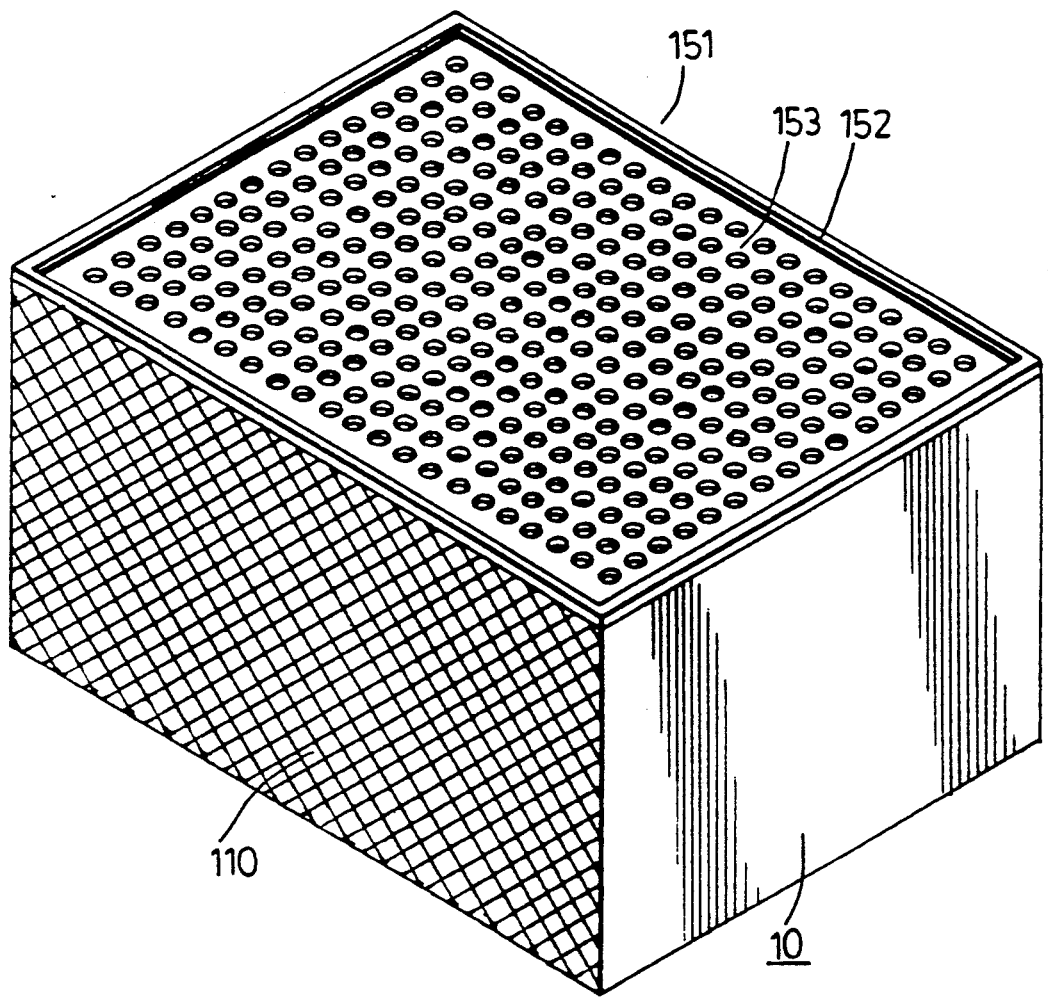
FIG. 5 is a rear perspective view of the first preferred embodiment.
Figure 5A:
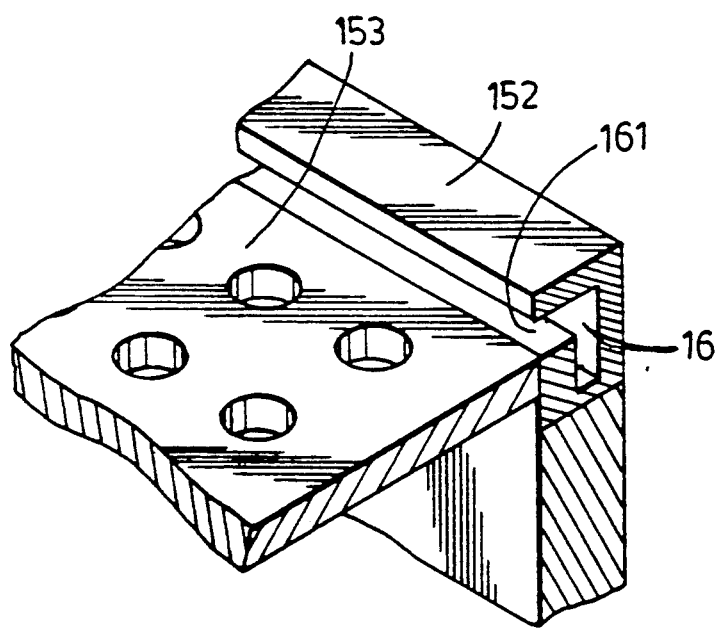
FIG. 5A is an enlarged view of a loop frame of a tabletop of the first preferred embodiment.

The workbench (10) further comprises a tabletop (151) having a hollow rectangular loop frame (152) mounted on an open top end defined by the four confining walls (15) of the workbench (10), and a flat table surface (153) mounted on an inner periphery of the loop frame (152). The table surface (153) has a perforated portion disposed directly on top of the larger chamber (111). The loop frame (152) confines an air passage (16) and has a notch (17) which communicates the air passage (16) and the smaller chamber (112), and an elongated outlet (161) which communicates the air passage (16) and the surrounding atmosphere (Refer to FIG. 5A).

A rear one of the confining walls (15) is provided with a sound muffling means (110). The sound muffling means (110) includes several layers of non-woven cloth so as to minimize the noise produced by the dust arrester of the present invention.

The filter unit (20), the first preferred embodiment is shown to have two filter units (20), is provided inside the larger chamber (111) and includes a tubular filter net (22) having a closed end and an open end, and an annular mounting portion (21) provided on the open end of the filter net (22). The mounting portion (21) has an annular lip (23) which extends in a direction similar to that of the step portion (18). An annular engaging member (100), which is substantially C-shaped in cross-section, is used to rotatably join the lip (23) and the step portion (18). The mounting portion (21) is further provided with an inward annular flange (211) which extends into the peripheral groove (61) of the bearing members (60). The bearing members (60) thus support the filter unit (20) on one side of the plate (12). The mounting portion (21) also has external gear teeth (212) which are connected to the sprocket (71) of the driving unit (70) via a chain (80).

The driving unit (30) is mounted to the positioning plate (14) and extends into the filter unit (20). The driving unit (30) has a front and a rear output shaft (not shown). The rear output shaft extends into the smaller chamber (112) via the axle hole (141) of the positioning plate (14). The suction unit (40) is provided in the smaller chamber (112) and has a fan blade (41) rotatably driven by the rear output shaft of the driving unit (30). The blowing unit (50) is provided inside the filter unit (20) and has a fan blade (51) rotatably driven by the front output shaft of the driving unit (30). The blowing unit (50) is further provided with a downwardly oriented air outlet (52). The air outlet (52) is substantially cone-shaped and has an elongated mouth which extends in the axial direction of the filter unit (20).

The operation of the first preferred embodiment is as follows: When the driving unit (70) is activated, the sprocket (71) rotatably drives the chain (80) to cause axial rotation of the filter units (20). The filter units (20) are rotatably supported on the mounting plate (12) by the flange (211) of the filter units (20) which extends into the peripheral groove (61) of the bearing members (60).

When the driving unit (70) is activated, the driving units (30) inside the filter units (20) are simultaneously activated. The output shafts of the driving unit (30) rotate the fan blades (41, 51) of the suction unit (40) and the blowing unit (50). The rotation of the fan blade (41) of the suction unit (40) draws polluted air through the perforated portion of the table surface (153) and into the larger chamber (111). Air in the larger chamber (111) enters the filter units (20) and flows through the through openings (13) of the plate (12). High pressure air enters the smaller chamber (112) via an air outlet (42) of the suction units (40).

Air is filtered as it passes through the filter units (20). The rotation of the fan blade (51) of the blowing unit (50) produces an air stream at the air outlet (52). The air stream at the air outlet (52) blows the dust particles collected by the respective filter unit (20) into one of the dust receiving bins (90).

Clean air is released by the first preferred embodiment in the following manner: A small portion of the air entering the smaller chamber (112) via the air outlet (42) of the suction units (40) flows through the notch (17) to enter the air passage (16) of the loop frame (152). Air inside the passage (16) is released to the surrounding atmosphere via the elongated outlet (161). A larger portion of the air inside the smaller chamber (112) flows through the sound muffling means (110). The air stream at the elongated outlet (161) directs polluted air towards the center of the tabletop (151) and at the same time, prevents dust particles from collecting on the table surface (153).

Note that the dust arrester of the present invention is simple in construction, is easy to construct, and can effectively control air pollution at a relatively lower cost. A portion of the clean air output of the suction unit (40) is also used to direct polluted air towards the center of the tabletop (151) and to prevent (153).

Figure 6:
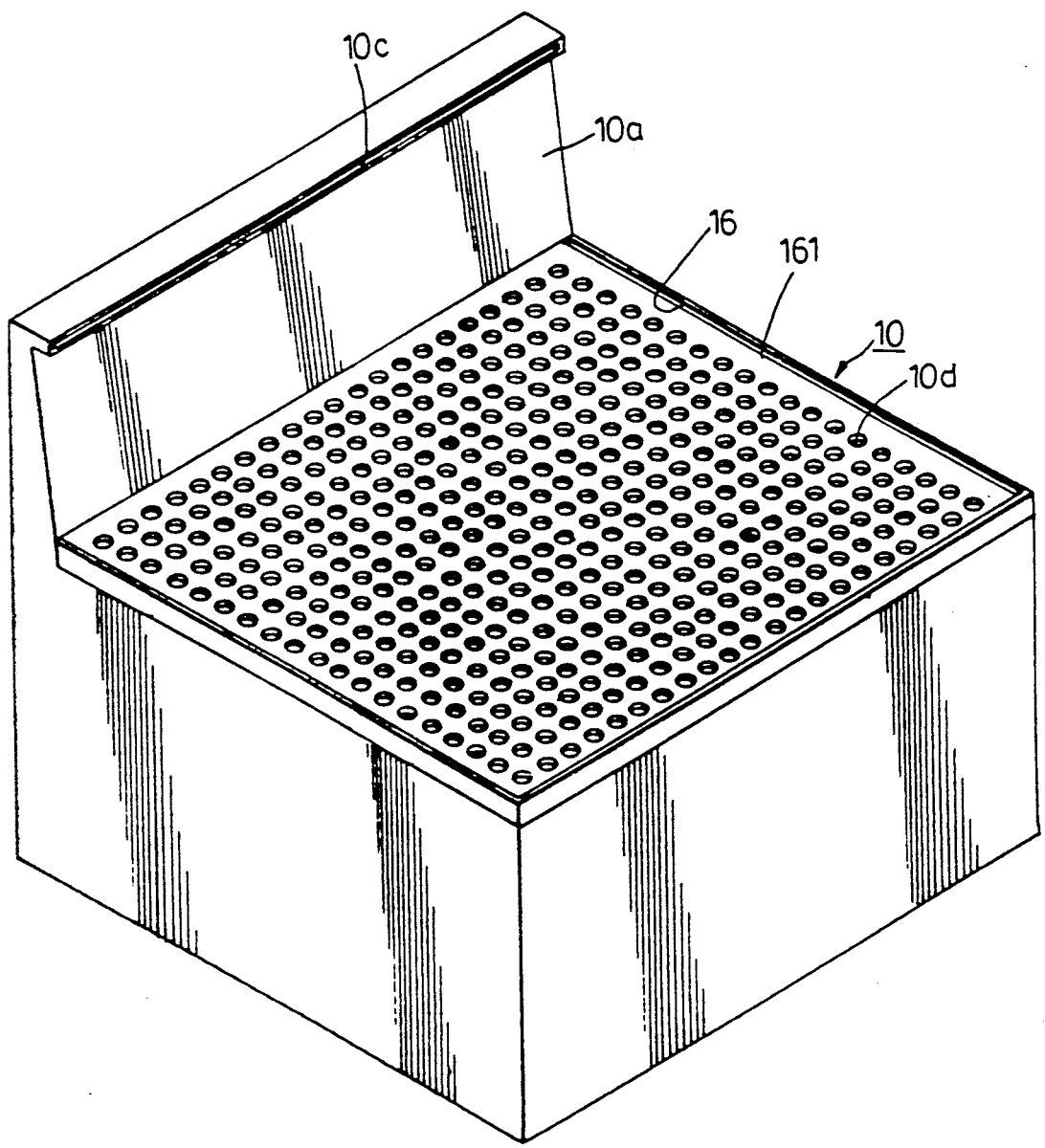
FIG. 6 is a front perspective view of the second preferred embodiment of a dust arrester according to the present invention.
Figure 7:
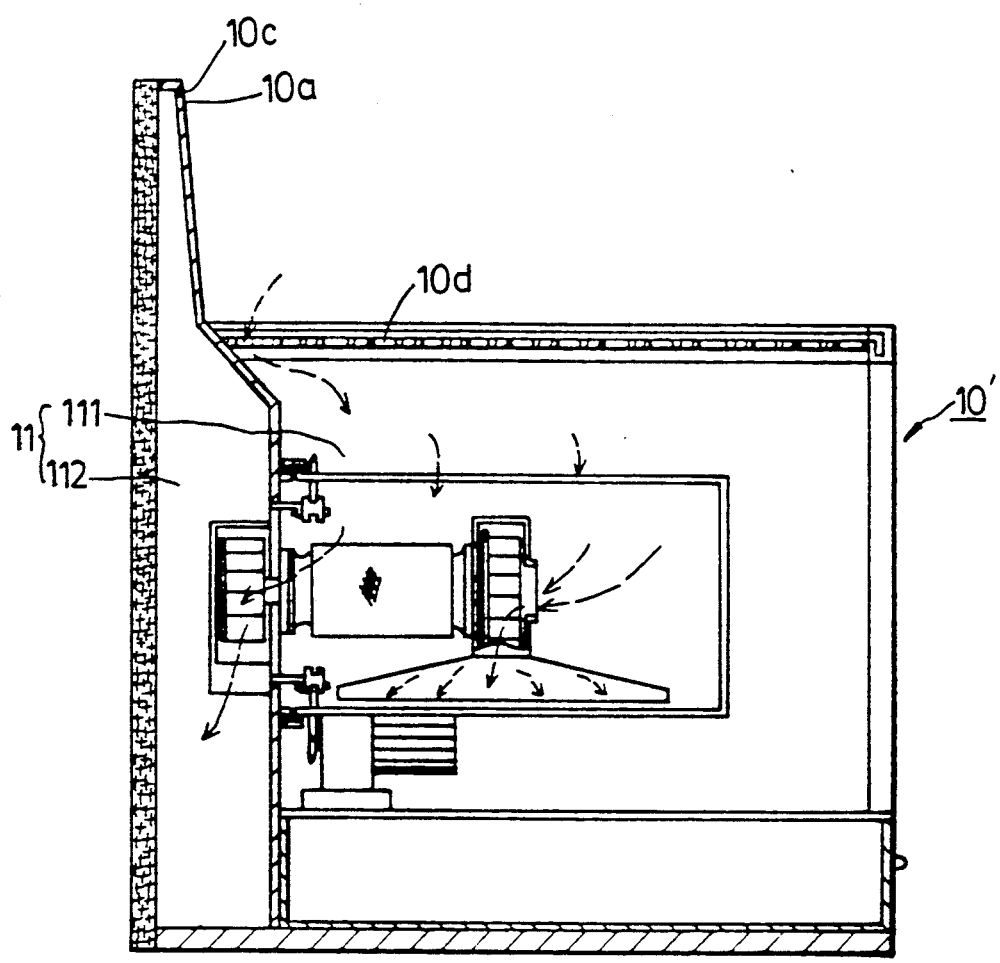
FIG. 7 is a side view of the second preferred embodiment.

Referring to FIGS. 6 and 7, the second preferred embodiment of a dust arrester according to the present invention is shown to be substantially similar to the first preferred embodiment. The workbench (10') of the second preferred embodiment, however, includes an upwardly extending conduit (10a) which is communicated with the smaller chamber (112). The conduit (10a) has a top end provided with an elongated outlet (10c). As with the first preferred embodiment, the workbench (10') has a tabletop provided with a perforated portion (10d) that is disposed directly on top of the larger chamber (111). The tabletop also has an air passage (16) and an elongated outlet (161). The operation of the second preferred embodiment is similar to that of the first preferred embodiment and will not be detailed further.

While the present invention has been described in connection with what is considered the most practical and preferred embodiments, it is understood that this invention is not limited to the disclosed embodiments, but is intended to cover various arrangements included within the spirit and scope of the broadest interpretation so as to encompass all such modifications and equivalent arrangements.

I claim:

1. A dust arrester for a sanding machine, comprising:
   a hollow workbench including: a confining wall that defines a receiving space and having an open top end, a front side and a rear side; an upright mounting plate provided inside said confining wall between said front side and said rear side, said mounting plate partitioning said receiving space into a first chamber and a second chamber, said mounting plate being formed with an enlarged through opening; a diametrically extending positioning plate of predetermined width being mounted on said mounting plate at said through opening; a tabletop including a hollow loop frame mounted on said open top end of said confining wall and having an inner periphery, and a flat table surface mounted on said inner periphery of said loop frame, said table surface having a perforated portion disposed directly on top of said first chamber, said loop frame confining an air passage and having a notch communicating said second chamber and said air passage, and an elongated outlet communicating said air passage and the surrounding atmosphere; a removable dust receiving means provided at a bottom end of said first chamber; and a sound muffling unit provided inside said second chamber at said rear side of said confining wall;
   a tubular filter unit being provided inside said first chamber and including a tubular filter net having a closed end and an open end, and an annular mounting portion provided on said open end of said filter net and being rotatably mounted on said mounting plate around said through opening;
   a first driving unit provided inside said first chamber and axially rotating said filter unit;
   a second driving unit mounted to said positioning plate and extending into said filter unit, said second driving unit having a front output shaft and a rear output shaft, said rear output shaft extending into said second chamber through said positioning plate;
   a blowing unit being provided inside said filter unit and having a downwardly oriented air outlet with an elongated mouth that extends in the axial direction of said filter unit, said blowing unit further having a fan blade being rotated by said front output shaft of said second driving unit so as to generate an air stream at said air outlet to blow dust particles collected by said filter net into said dust receiving means; and
   a suction unit being provided inside said second chamber and having a fan blade rotatably driven by said rear output shaft of said second driving unit so as to draw polluted air into said first chamber via said perforated portion of said table surface.

2. The dust arrester as claimed in claim 1, wherein said removable dust receiving means comprises a drawer-type dust receiving bin associated with said confining wall and slidably extending into said first chamber.

3. The dust arrester as claimed in claim 1, wherein said sound muffling means comprises several layers of non-woven cloth to permit the passage of a portion of air filtered by said filter unit and entering said second chamber to the surrounding atmosphere.

4. The dust arrester as claimed in claim 1, wherein said first chamber is larger than said second chamber.

5. The dust arrester as claimed in claim 1, wherein said workbench has an upwardly extending conduit communicated with said second chamber and disposed adjacent to said rear side of said confining wall, said conduit having a top end provided with an elongated outlet.

* * * * *

UNITED STATES PATENT AND TRADEMARK OFFICE
CERTIFICATE OF CORRECTION

PATENT NO.   :   5,131,192

DATED        :   July 21, 1992

INVENTOR(S)  :   Mau-Nan Cheng

It is certified that error appears in the above-identified patent and that said Letters Patent is hereby corrected as shown below:

```
Col. 4, line 58:
after "prevent" and before "(153)" insert --the
dust particles from collecting on the table
surface--.
```

Signed and Sealed this

Tenth Day of August, 1993

Attest:

MICHAEL K. KIRK

Attesting Officer

Acting Commissioner of Patents and Trademarks